(12) United States Patent
Ryu et al.

(10) Patent No.: US 8,203,031 B2
(45) Date of Patent: Jun. 19, 2012

(54) TRANSGENIC PLANTS EXHIBITING INCREASED RESISTANCE TO BIOTIC AND ABIOTIC STRESSES AND METHODS FOR PRODUCING THE SAME

(75) Inventors: Stephen Beungtae Ryu, Ochang-eup (KR); Hyoung-Yool Lee, Ochang-eup (KR); In-Whan Hwang, Pohang-si (KR); P. Palta Jiwan, Madison, WI (US)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 136 days.

(21) Appl. No.: 12/527,323

(22) PCT Filed: Feb. 15, 2008

(86) PCT No.: PCT/KR2008/000912
§ 371 (c)(1),
(2), (4) Date: Aug. 14, 2009

(87) PCT Pub. No.: WO2008/100112
PCT Pub. Date: Aug. 21, 2008

(65) Prior Publication Data
US 2010/0100984 A1   Apr. 22, 2010

Related U.S. Application Data

(60) Provisional application No. 60/890,191, filed on Feb. 16, 2007.

(51) Int. Cl.
*A01H 3/00* (2006.01)
*A01H 5/00* (2006.01)

(52) U.S. Cl. .................................... 800/279; 800/281
(58) Field of Classification Search .................. None
See application file for complete search history.

(56) References Cited

FOREIGN PATENT DOCUMENTS
EP        1033405 A2 *    9/2000

OTHER PUBLICATIONS

Lee et al, Multiple forms of secretory phospholipase A2 in plants, 2005, Progress in Lipid Research, 44, p. 52-67.*
Lee et al (Progress in Lipid Research 44 (2005) 52-67).*
Lee et al (The Plant Cell, vol. 15, 1990-2002, Sep. 2003).*
Kim et al (Biochimica et Biophysica Acta 1489 (1999) 389-392).*

\* cited by examiner

*Primary Examiner* — Anne Grunberg
*Assistant Examiner* — Lee Visone
(74) *Attorney, Agent, or Firm* — Clark & Elbing LLP

(57) ABSTRACT

The invention relates to plants, especially transgenic plants, plant parts and plant cells overproducing a secretory phospholipase A2 protein (e.g. sPLA2-a or sPLA2-b) and having an enhanced resistance against a wide range of abiotic (e.g., against osmotic stress) and biotic stress (e.g., bacterial, or fungal infections) conditions as well as inducing early flowering. The invention also comprises nucleic acid sequences encoding a secretory phospholipase A2 or functional isoforms thereof and the use of such sequences for rendering plants resistant against abiotic and biotic stress conditions. The invention is useful for mitigating crop damages by a wide variety of pathogen infections and stress conditions and for accelerating flowering time.

5 Claims, 9 Drawing Sheets

Mock    sPLA$_2$-a

SEQUENCE LISTING

<160> NUMBER OF SEQ ID NOS: 7

<210> SEQ ID NO 1
<211> LENGTH: 447
<212> TYPE: DNA
<213> ORGANISM: Arabidopsis thaliana

<400> SEQUENCE: 1

```
atggcggctc cgatcatact tttctctttc cttttattct tctctgtctc tgtctcggca      60
cttaacgtcg gtgttcagct catacatccc tccatttcct tgactaaaga atgtagccgg     120
aaatgtgaat cagagttttg ttcagtgcct ccatttctga ggtatgggaa gtactgtgga     180
ctactttaca gtggatgtcc tggtgagaga ccttgtgatg gtcttgattc ttgttgcatg     240
aaacatgatg cttgtgtcca atccaagaat aatgattatc taagccaaga gtgtagtcag     300
aagttcatta actgcatgaa caatttcagc cagaagaagc aaccgacgtt caaaggtaac     360
aaatgcgacg ctgatgaagt gattgatgtc atctccattg tcatggaagc tgctcttatc     420
gccggcaaag tcctcaagaa accctaa                                         447
```

<210> SEQ ID NO 2
<211> LENGTH: 148
<212> TYPE: PRT
<213> ORGANISM: Arabidopsis thaliana

<400> SEQUENCE: 2

```
Met Ala Ala Pro Ile Ile Leu Phe Ser Phe Leu Leu Phe Phe Ser Val
  1               5                  10                  15

Ser Val Ser Ala Leu Asn Val Gly Val Gln Leu Ile His Pro Ser Ile
             20                  25                  30

Ser Leu Thr Lys Glu Cys Ser Arg Lys Cys Glu Ser Glu Phe Cys Ser
         35                  40                  45

Val Pro Pro Phe Leu Arg Tyr Gly Lys Tyr Cys Gly Leu Leu Tyr Ser
     50                  55                  60

Gly Cys Pro Gly Glu Arg Pro Cys Asp Gly Leu Asp Ser Cys Cys Met
 65                  70                  75                  80

Lys His Asp Ala Cys Val Gln Ser Lys Asn Asn Asp Tyr Leu Ser Gln
                 85                  90                  95

Glu Cys Ser Gln Lys Phe Ile Asn Cys Met Asn Asn Phe Ser Gln Lys
            100                 105                 110

Lys Gln Pro Thr Phe Lys Gly Asn Lys Cys Asp Ala Asp Glu Val Ile
        115                 120                 125

Asp Val Ile Ser Ile Val Met Glu Ala Ala Leu Ile Ala Gly Lys Val
    130                 135                 140
```

Leu Lys Lys Pro
145

<210> SEQ ID NO 3
<211> LENGTH: 444
<212> TYPE: DNA
<213> ORGANISM: Arabidopsis thaliana

<400> SEQUENCE: 3

```
atgatgtttc gcacttcatt gatgcgtttc gcggcagctt tcttcgccat tgtcttcgtc      60
gttctcgtcg gtgtcgctcg cagtgaggag tgtacaagaa cttgcattgc acagaattgt     120
gacactcttt ctattcgata tgggaagtat tgtgggattg gacattctgg ttgtcctggt     180
gaggagcctt gtgatgatct tgatgcttgt gtaagatcc atgaccattg tgttgagtta      240
aacggtatga ctaacataag ctgccataag aagttccagc gatgcgtaaa caggctaagc     300
aaagcgataa acagtctaa aaacaaaaag gttggatttt ccacaaagtg cccttattca      360
gtagtcatac ctacggtgaa tcaaggaatg gatattggaa tcttattcag tcaattaggt     420
aatgatatga aacagagct atga                                             444
```

<210> SEQ ID NO 4
<211> LENGTH: 147
<212> TYPE: PRT
<213> ORGANISM: Arabidopsis thaliana

<400> SEQUENCE: 4

Met Met Phe Arg Thr Ser Leu Met Arg Phe Ala Ala Phe Phe Ala
1               5                   10                  15

Ile Val Phe Val Val Leu Val Gly Val Ala Arg Ser Glu Glu Cys Thr
                20                  25                  30

Arg Thr Cys Ile Ala Gln Asn Cys Asp Thr Leu Ser Ile Arg Tyr Gly
            35                  40                  45

Lys Tyr Cys Gly Ile Gly His Ser Gly Cys Pro Gly Glu Glu Pro Cys
        50                  55                  60

Asp Asp Leu Asp Ala Cys Cys Lys Ile His Asp His Cys Val Glu Leu
65                  70                  75                  80

Asn Gly Met Thr Asn Ile Ser Cys His Lys Lys Phe Gln Arg Cys Val
                85                  90                  95

Asn Arg Leu Ser Lys Ala Ile Lys Gln Ser Lys Asn Lys Lys Val Gly
            100                 105                 110

Phe Ser Thr Lys Cys Pro Tyr Ser Val Val Ile Pro Thr Val Asn Gln
        115                 120                 125

Gly Met Asp Ile Gly Ile Leu Phe Ser Gln Leu Gly Asn Asp Met Lys
    130                 135                 140

Thr Glu Leu
145

<210> SEQ ID NO 5
<211> LENGTH: 30
<212> TYPE: PRT
<213> ORGANISM: Arabidopsis thaliana

<400> SEQUENCE: 5

Arg Tyr Gly Lys Tyr Cys Gly Leu Leu Tyr Ser Gly Cys Pro Gly Glu
1               5                   10                  15

Arg Pro Cys Asp Gly Leu Asp Ser Cys Cys Met Lys His Asp
                20                  25                  30

```
<210> SEQ ID NO 6
<211> LENGTH: 18
<212> TYPE: DNA
<213> ORGANISM: Artificial Sequence
<220> FEATURE:
<223> OTHER INFORMATION: Synthetic Construct

<400> SEQUENCE: 6
tcgcacttca ttgatgcg                                                   18

<210> SEQ ID NO 7
<211> LENGTH: 28
<212> TYPE: DNA
<213> ORGANISM: Artificial Sequence
<220> FEATURE:
<223> OTHER INFORMATION: Synthetic Construct

<400> SEQUENCE: 7
tcatagctct gttttcatat cattacct                                        28
```

US 8,203,031 B2

TRANSGENIC PLANTS EXHIBITING INCREASED RESISTANCE TO BIOTIC AND ABIOTIC STRESSES AND METHODS FOR PRODUCING THE SAME

CROSS-REFERENCE TO RELATED APPLICATIONS

This application claims priority under 35 U.S.C. §371 from international application PCT/KR2008/000912, filed Feb. 15, 2008, which claims priority from U.S. Patent Application No. 60/890,191, filed Feb. 16, 2007.

TECHNICAL FIELD

The present invention relates to plants, especially transgenic plants, plant parts and plant cells overproducing a secretory phospholipase A2 (sPLA2) protein and having an enhanced resistance against a wide range of abiotic and biotic stress conditions as well as inducing early flowering. The invention also comprises nucleic acid sequences encoding a sPLA2 or functional variants thereof and the use of said sequences for rendering plants resistant against abiotic and biotic stress conditions as well as early flowering.

BACKGROUND ART

During their different developmental stages, plants are exposed to an extremely wide range of biotic and abiotic stress conditions. The injury of crops as a result of abiotic and biotic stresses has been a major problem in the agricultural production areas. It is, thus, a very important task of high economic significance to develop new crops of simultaneously enhanced resistances against both abiotic and biotic stresses. Most functional genes have been limited on only one of those aspects. Recent trend is to find multifunctional genes that protect plant from both abiotic and biotic stresses. There are a few examples of multifunctional genes including "ferritin" gene that induces an enhanced resistance against a wide range of abiotic and biotic oxidative stress conditions (U.S. Pat. No. 6,563,019). However, there is almost no example of multifunctional gene that induces an enhanced resistance against abiotic and biotic stresses as well as an early flowering. All of those aspects are of significant factors in agricultural crop improvement.

There exists a continuing need to develop plants and crops that exhibit improved resistance to plant stresses, thereby increasing crop yields in adverse conditions and reducing the risk of crop failure. For example, plants with increased tolerance to drought, extreme temperatures and higher salt conditions may open the possibility of farming in semi-desert climates, where agriculture was previously non-viable. In addition, the development of novel crops with improved tolerance to cold or freezing temperatures may significantly prolong the growing season in regions with colder climates.

A number of plant genes are known to show increased levels of expression when plants are exposed to stress. However, despite considerable efforts to engineer genetically modified crops with increased stress tolerance, to date there are little or no such crops on the commercial market.

The future prospects of engineering novel plants with an increased capacity to tolerate environmental insults will depend on the modulation of critical stress tolerance controlling genes, and knowledge of their functional regulatory properties. The inventors for the present application, and others, have endeavored to decipher the mechanisms of plant stress tolerance in the hope of developing an understanding of the biochemical pathways involved. Nonetheless, the characterization of the genes and proteins involved in plant stress responses presents a number of significant challenges.

There remains a continuing need to develop a better understanding of plant stress responses, so that corresponding methods can be developed to confer advantageous properties to plants. This need extends to the production of crops that exhibit resistance to damage by adverse climatic conditions such as excessive temperatures, drought, and conditions of high salinity. Even incremental gains in plant stress tolerance may have a significant economic impact in stablizing the quality and supply of grain, oilseed and horticulture. Enhancement of germination, growth and flowering are extremely important in regions that have a short or otherwise difficult growing season.

In the *Arabidopsis* genome, there are two different groups of $PLA_2$: 1) the secretory low molecular weight $PLA_2$ (sPLA2) and 2) the patatin-like nonspecific PLAs which have combined $PLA_1$ and $PLA_2$ activities. Four low molecular weight $PLA_2$ isoforms and 10 members of patatin-like PLAs have been found from the *Arabidopsis* genomic sequence database (Ryu et al., 2005 Progress in Lipid Research).

In order to identify multifunctional isoform(s) of PLA2, we have first focused on the four isoforms of sPLA2s, because the former are genuine PLA2s and are predicted to be secreted into endoplasmic reticulum and further into extracellular spaces and vacuoles. Endoplasmic reticulum and extracellular spaces have been proved to be key regulatory locations of multifunctional signaling in plants and animals. Among four isoforms of sPLA2, only sPLA2-a and sPLA2-b genes are expressed throughout whole plant tissues. On the other hand, sPLA2-e and sPLA2-g are found to be only expressed in flower tissues. The plant overexpressing a sPLA2-a or sPLA2-b protein exhibited an enhanced resistance against abiotic and biotic stresses. Interestingly, the transgenic plants overproducing sPLA-b protein also exhibited a phenotype of accelerated flowering time. Up to date, there is no report, to our best knowledge, that a gene simultaneously enhances three different aspects of agricultural traits such as resistance against both abiotic and biotic stresses as well as accelerated flowering time. It is noteworthy that a nonspecific patatin-like PLA has been found to be involved in the defense reaction of plants against attacks of pathogens (WO0183788).

In order to overcome above-mentioned problems of conventional methods, the present inventors have tried to develop plants and crops that exhibit improved resistance to plant stresses. Then, we have identified that commercially desired plants that have enhanced ability of flowering and more resistance against abiotic and biotic stresses can be produced by manipulating expression of sPLA2 gene in transgenic plants and completed the present invention successfully.

Throughout this application, several patents and publications are referenced or cited in parentheses. The disclosure of these patents and publications is incorporated into this application in order to more fully describe this invention and the state of the art to which this invention pertains.

DISCLOSURE OF INVENTION

It is an object of the present invention to provide a novel and general method suitable to provide crops, especially transgenic crops, with enhanced resistance against a wide range of both abiotic and biotic stress conditions as well as with accelerated flowering time.

It is another object of the present invention to provide crops and breeding material, advantageously transgenic plant, having increased resistance against a wide range of both abiotic and biotic stress conditions and induced early flowering.

Other objects and advantage of the present invention will become apparent from the detailed description to follow taken in conjugation with the appended claims and drawings.

The approach of the present invention is that overproducing or ectopically expressing sPLA2 or sPLA2-like proteins, e.g. transferring, in different organs of plants will increase the intracellular lysophospholipid concentration and, therefore, reduce the damaging effects of abiotic and biotic stresses and accelerate flowering.

Therefore, to achieve the above-defined objects of the invention we have cloned four different sPLA2 isoform genes (sPLA2-a, sPLA2-b, sPLA2-e, sPLA2-g) from *Arabidopsis thaliana* Col-0 ecotype and overproduced it in the tissues of *Arabidopsis* plants.

We have found that the transgenic plants overexpressing sPLA2-a (sPLA2-alpha) or sPLA2-b (sPLA2-beta) gene, which is expressed throughout whole plant tissues, exhibit an enhanced resistance against abiotic and biotic stresses. In addition, the transgenic plants overproducing sPLA-b proteins exhibited a phenotype of early flowering. On the other hand, sPLA2-e and sPLA2-g are found to be only expressed in flower tissues. It was also found that both sPLA2-a and sPLA2-b proteins itself show anti-fungal activities in in vitro assay (Example 3).

The present invention, therefore, provides plants overexpressing a sPLA2-a and/or sPLA2-b protein and having an enhanced resistance against abiotic and biotic stresses in addition to an accelerated flowering time. The plants according to the invention are advantageously transgenic cells transformed by the introduction of a nucleic acid, e.g. in the form of vector, coding for the expression of a sPLA2 protein, advantageously sPLA2-a and/or sPLA2-b.

According to preferred embodiments of the invention, there are provided plant cells which are overproducing a sPLA2 having the amino acid sequence of SEQ ID No 2 and/or SEQ ID No 4 as shown in the attached sequence listing, or a functional variant thereof, said functional variant being advantageously at least 70%, and more advantageously at least 80% and even more advantageously at least 85% homologous in catalytic motifs to said sPLA2 polypeptide as shown in SEQ ID No. 5.

The invention further provides plants, advantageously transgenic plants, and parts thereof comprising cells according to the invention. Plant, plant parts or plant cells according to the invention advantageously have an enhanced resistance against abiotic stresses including salt stress and/or infections of bacterial or fungal origin and an accelerated flowering time.

The invention also comprises the use of the polypeptides containing the conserved amino acid sites of sPLA2 (SEQ ID No:5) for the preparation of plant cells, plant parts and plants according to the invention.

The present disclosure and examples below demonstrate that synthesis of the sPLA2 protein in vegetative tissues of plants provides resistance against abiotic and biotic stresses as well as early flowering. This novel technology according to the present invention based on ectopic expression of sPLA2-a and/or sPLA2-b proteins, therefore, potentially has high agronomic significance in that it may reduce primary membrane damage in crops caused by either biotic or abiotic stress conditions and also accelerate flowering time.

The invention is useful for mitigating crop damages by a wide variety of stress conditions and pathogen infections and accelerating recovery of crops injured and inducing early flowering.

With respect to the present specification and claims, we will use the following technical terms in accordance with the given definitions. With regard to the interpretation of the present invention, it shall be understood that the below defined terms are used in accordance with the given definitions even if said definitions might not be in perfect harmony with the usual interpretation of said technical term.

A "polynucleotide" is a sequence of two or more deoxyribonucleotides (in DNA) or ribonucleotides (in RNA).

A "polypeptide" is an amino acid sequence comprising a plurality of consecutive polymerized amino acid residues e.g., at least about 15 consecutive polymerized amino acid residues.

A "recombinant polypeptide" is a polypeptide produced by translation of a recombinant polynucleotide. A "synthetic polypeptide" is a polypeptide created by consecutive polymerization of isolated amino acid residues using methods well known in the art.

A "recombinant polynucleotide", for instance a recombinant DNA molecule, is a novel nucleic acid sequence formed through the ligation of two or more nonhomologous DNA molecules (for example a recombinant plasmid containing one or more inserts of foreign DNA cloned into it).

"Expression" refers to the transcription of a gene into structural RNA (rRNA, tRNA) or messenger RNA (mRNA) with subsequent translation into a protein in the case of the mRNA.

Two DNA sequences are "operably linked" if the linkage allows the two sequences to carry out their normal functions relative to each other. For instance, a promoter region would be operably linked to a coding sequence if the promoter were capable of effecting transcription of that coding sequence and said coding sequence encoded a product intended to be expressed in response to the activity of the promoter.

A "promoter" or transcriptional regulatory region is a cis-acting DNA sequence, generally located upstream of the initiation site of a gene, to which RNA polymerase may bind and initiate correct transcription.

"Transformation" means the directed modification of the genome of a cell by the external application of recombinant DNA from another cell of different genotype, leading to its uptake and integration into the subject cell's genome.

A "functional variant" of a protein is a polypeptide the amino acid sequence of which can be derived from the amino acid sequence of the original protein by the substitution, deletion and/or addition of one or more amino acid residue in a way that, in spite of the change in the amino acid sequence, the functional variant retains at least a part of at least one of the biological activities of the original protein that is detectable for a person skilled in the art. A functional variant is generally at least 70% homologous, advantageously at least 80% homologous and even more advantageously at least 85% homologous in catalytic motifs (shown in SEQ ID NO:5) such as calcium binding loop and active site to the protein from which it can be derived. Any functional part of a protein or a variant thereof is also termed functional variant.

The percentage of homology or similarity is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity.

Optimal alignment of sequences for comparison may be conducted by computerized implementations of known algorithms, or by inspection. Readily available sequence comparison and multiple sequence alignment algorithms are, respectively, the Basic Local Alignment Search Tool (BLAST) (Altschul, S. F. et al 1990. J. Mol. Biol. 215:403; Altschul, S. F. et al 1997. Nucleic Acids Res. 25: 3389-3402) and ClustalW programs. BLAST is available at the website of the National Center for Biotechnology Information (NCBI) and a version of ClustalW is available at the website of the European Bioinformatics Institute (EBI). Other suitable programs include GAP, BESTFIT, FASTA, and TFASTA in the Wisconsin Genetics Software Package (Genetics Computer Group (GCG), 575 Science Dr., Madison, Wis.). For greater certainty, as used herein and in the claims, "percentage of sequence identity" or "percentage of sequence homology" of amino acid sequences is determined based on optimal sequence alignments determined in accordance with the default values of the BLASTX program, available as described above.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat), fruit (the mature ovary), plant tissue (for example, vascular tissue or ground tissue), cells (for example, guard cells, egg cells, and the like), and progeny of plants. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (as shown in FIG. 1, adapted from Daly et al. (2001) Plant Physiol. 127: 1328-1333; FIG. 2, adapted from Ku et al. (2000) Proc. Natl. Acad. Sd. USA 97: 9121-9126; and also Tudge in The Variety of Life. Oxford University Press, New York, N.Y. (2000) pp. 547-606).

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell. "Wild type" or "wild-type", as used herein, refers to a plant cell, seed, plant component, plant tissue, plant organ or whole plant that has not been genetically modified or treated in an experimental sense.

A plant, plant part, a plant tissue or a plant cell is said to have an "enhanced resistance" against a damaging effect, eg. damaging agent, if it can tolerate a significantly and detectably (e.g. at least 20%) stronger damaging effect, eg. dose or intensity of damaging agent, of the same type, without suffering any detectable damage, than its natural counterpart would do.

Within the framework of the present description a "secretory phospholipase A2 (sPLA2)" is defined, as it is usual in the art, as a protein that is secreted in endoplasmic reticulum or extracellular spaces and capable of hydrolyzing phospholipids to generate lysophospholipids and free fatty acids (Reviewed by Ryu, S. B. 2004 Trends in Plant Sci. 9:229-235). The members of the sPLA2 family are highly conserved both in their amino acid sequence in catalytic motifs (SEQ ID NO:5) including calcium binding loop and active site.

The term "abiotic and biotic stresses" is used in very general sense comprising several kinds of abiotic (e.g. treatment with different chemical agents or exposure to extreme environmental conditions such as high salt, high or low temperature or drought) and biotic stress (e.g. infection with bacteria, fungus or virus) conditions in the manifestation of damaging effects.

Hereinafter, the present invention will be described more clearly as follows.

In one aspect of the present invention, there is provided a transgenic plant transformed with an expression vector comprising a polynucleotide encoding a sPLA2 protein having a amino acid sequence of SEQ ID NO:2 or SEQ ID NO:4 or a functional variant thereof; wherein the expression vector further comprises a regulatory element operably linked to the polynucleotide; and the expression level of the sPLA2 protein in the transgenic plant is higher than that of an untransformed wild type plant. The SEQ ID NO:1 and SEQ ID NO:2 correspond to the nucleotide sequence and deduced amino acid sequence of sPLA2-a cDNA. The SEQ ID NO:3 and SEQ ID NO:4 correspond to the nucleotide sequence and deduced amino acid sequence of sPLA2-b cDNA.

In a preferred embodiment of the transgenic plant, the functional variant of the sPLA2 protein may comprise a catalytic motif having at least 80% sequence homology with SEQ ID NO:5.

In a preferred embodiment of the transgenic plant, the polynucleotide may comprise a nucleotide sequence of SEQ ID NO:1 or SEQ ID NO:3.

In a preferred embodiment of the transgenic plant, the regulatory element may be selected from the group consisting of an constitutive promoter, an inducible promoter, a strong promoter, a weak promoter, a tissue specific promoter, a tissue-inspecific promoter, and organ specific promoter, a cell-specific promoter. More preferably the regulatory element is a constitutive promoter for overexpressing said polynucleotide encoding a sPLA2 protein. More preferably the expression vector may be the pBIG-HYG vector under the control of the CaMV 35S promoter as depicted in FIG. 1.

In a preferred embodiment of the transgenic plant, the transgenic plant may be more resistant to abiotic and biotic stresses than an untransformed wild type plant.

In a preferred embodiment of the transgenic plant, the transgenic plant may be resistant to at least one fungal disease.

In a preferred embodiment of the transgenic plant, the transgenic plant may resistant to the genus *Fusarium, Botrytis, Alternaria,* or *Peronospora.*

In a preferred embodiment of the transgenic plant, the transgenic plant may be resistant to more than one bacterial pathogen or disease.

In a preferred embodiment of the transgenic plant, the transgenic plant may be resistant to the genus *Pseudomonas* or *Erwinia.*

In a preferred embodiment of the transgenic plant, the transgenic plant may be tolerant to at least one abiotic stress.

In a preferred embodiment of the transgenic plant, the transgenic plant may be more tolerant to high salt-induced osmotic stress.

In a preferred embodiment of the transgenic plant, the transgenic plant may have an earlier flowering time.

In another aspect of the present invention, there is provided a method for producing a transgenic plant having a resistance to abiotic and biotic stresses and/or an early flowering time, which comprises the steps of:
(a) transforming a target plant with an expression vector comprising a polynucleotide encoding a sPLA2 protein having a amino acid sequence of SEQ ID NO:2 or SEQ ID NO:4 or a functional variant thereof; wherein the expression vector further comprises a regulatory element operably linked to the polynucleotide; and
(b) selecting a transgenic plant that is more resistant to the abiotic and biotic stresses and/or has an earlier flowering time than an untransformed wild type plant.

In a preferred embodiment of the method for producing a transgenic plant, the functional variant of the sPLA2 protein may comprise a catalytic motif having at least 80% sequence homology with SEQ ID NO:5.

In a preferred embodiment of the method for producing a transgenic plant, the polynucleotide may comprise a nucleotide sequence of SEQ ID NO:1 or SEQ ID NO:3.

In a preferred embodiment of the method for producing a transgenic plant, the regulatory element may be selected from the group consisting of an constitutive promoter, an inducible promoter, a strong promoter, a weak promoter, a tissue specific promoter, a tissue-inspecific promoter, and organ specific promoter, a cell-specific promoter. More preferably the regulatory element is a constitutive promoter for overexpressing said polynucleotide encoding a sPLA2 protein. More preferably the expression vector may be the pBIG-HYG vector under the control of the CaMV 35S promoter as depicted in FIG. 1.

In another aspect of the present invention, there is provided a method for increasing the resistance to abiotic and biotic stresses of a plant, which comprises the steps of:
(a) transforming a target plant with an expression vector comprising a polynucleotide encoding a sPLA2 protein having a amino acid sequence of SEQ ID NO:2 or SEQ ID NO:4 or a functional variant thereof; wherein the expression vector further comprises a regulatory element operably linked to the polynucleotide; and
(b) selecting a transgenic plant that is more resistant to the abiotic and biotic stresses than an untransformed wild type plant.

In a preferred embodiment of the method for increasing the resistance to abiotic and biotic stresses of a plant, the polynucleotide may comprise a nucleotide sequence of SEQ ID NO:1 or SEQ ID NO:3.

In another aspect of the present invention, there is provided a method for accelerating the flowering time of a plant, which comprises the steps of:
(a) transforming a target plant with an expression vector comprising a polynucleotide encoding a sPLA2 protein having a amino acid sequence of SEQ ID NO:2 or SEQ ID NO:4 or a functional variant thereof; wherein the expression vector further comprises a regulatory element operably linked to the polynucleotide; and
(b) selecting a transgenic plant that has an earlier flowering time than an untransformed wild type plant.

In a preferred embodiment of the method for accelerating the flowering time of a plant, the polynucleotide may comprise a nucleotide sequence of SEQ ID NO:3.

In another aspect of the present invention, there is provided a seed produced by a transgenic plant made by the method of any of claims 13-15, wherein the seed comprises a polynucleotide encoding a sPLA2 protein having a amino acid sequence of SEQ ID NO:2 or SEQ ID NO:4 or a functional variant thereof.

In a preferred embodiment of the seed of the present invention, the polynucleotide may comprise a nucleotide sequence of SEQ ID NO:1 or SEQ ID NO:3.

In another aspect of the present invention, there is provided a composition for increasing the resistance to abiotic and biotic stresses of a plant, which comprises a sPLA2 protein having a amino acid sequence of SEQ ID NO:2 or SEQ ID NO:4 or a functional variant thereof.

In another aspect of the present invention, there is provided a method for increasing the resistance to abiotic and biotic stresses of a plant, which comprises the step of applying to a plant in need of the resistance an effective amount of a composition comprising a sPLA2 protein having a amino acid sequence of SEQ ID NO:2 or SEQ ID NO:4 or a functional variant thereof.

In another aspect of the present invention, there is provided a composition for accelerating the flowering time of a plant, which comprises a sPLA2 protein having a amino acid sequence of SEQ ID NO:4 or a functional variant thereof.

In another aspect of the present invention, there is provided a method for accelerating the flowering time of a plant, which comprises the step of applying to a plant in need of the accelerated flowering time an effective amount of a composition comprising a sPLA2 protein having a amino acid sequence of SEQ ID NO:4 or a functional variant thereof.

Preferably, the composition of the present invention contains an acceptable carrier for the sPLA2 protein, such as water. However, other carriers, such as organic solvents, can also be used. The amount of sPLA2 protein contained in the composition is an amount which is effective to prevent injury from abiotic and biotic stresses and/or accelerate the flowering time of a plant. Preferably, the amount of sPLA2 protein in the composition is in the range of from about 1.0 to about 400 mg per 1 liter of the composition according to the present invention.

The composition can be applied to the plant in any form. Preferably, the composition is applied as spray or simply dipping the plant in the solution.

The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts that describe molecular biological techniques useful herein, including the use and production of vectors, promoters and many other relevant topics, include Berger and Kimmel (1987) Guide to Molecular Cloning Techniques, Sambrook (1989) Molecular Cloning, and Ausubel (1997, 2000) Current Protocols in Molecular Biology. Any of the identified sequences can be incorporated into a cassette or vector, e.g., for expression in plants. A number of expression vectors suitable for stable transformation of plant cells or for the establishment of transgenic plants have been described including those described in Weissbach and Weissbach (1989) Methods for Plant Molecular Biology. Academic Press, and Gelvin et al. (1990) Plant Molecular Biology Manual. Kluwer Academic Publishers. Specific examples include those derived from a Ti plasmid of, Agrobacterium tumefaciens, as well as those disclosed by Herrera-Estrella et al. (1983) Nature 303: 209, Bevan (1984) Nucleic Acids Res. 12: 8711-8721, Klee (1985) Bio/Technology 3: 637-642, for dicotyledonous plants. Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) Bio/Technology 9: 957-962) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol. 102: 1077-1084; Vasil (1993) Bio/Technology 10: 667-674; Wan and Lemeaux (1994) Plant Physiol. 104: 37-48, and for Agrobacterium-mediated DNA transfer (Ishida et al. (1996) Nature Biotechnol. 14: 745-750).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter (e.g; a regulatory region controlling inducible or constitutive, environmentally- or developmentally-regulated, or cell- or tissue-specific expression), a transcription initiation start site, an RNA processing signal (such as intron splice sites), a transcription termination site, and/or a polyadenylation signal. The promoter sequences can be isolated according to methods known to one skilled in the art. Examples of constitutive plant promoters which can be useful for expressing the sPLA2 protein include: the cauliflower mosaic virus (CaMV) 35S promoter, which confers constitutive, high-level expression in most plant tissues (for example, Odell et al. (1985) Nature 313: 810-812); the nopaline synthase promoter (An et al. (1988) Plant Physiol. 88: 547-552); and the octopine synthase promoter (Fromm et al. (1989) Plant Cell 1: 977-984).

The polynucleotide of the invention may be operably linked with a specific promoter that causes the polynucleotide to be expressed in response to environmental, tissue-specific or temporal signals. A variety of plant gene promoters are known to regulate gene expression in response to environmental, hormonal, chemical, developmental signals, and in a tissue-active manner. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorably be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773, 697), fruit-specific promoters that are active during fruit ripening, such as the dru 1 promoter (U.S. Pat. No. 5,783,393), or the 2A1 1 promoter (U.S. Pat. No. 4,943,674) and the tomato polygalacturonase promoter (Bird et al. (1988) Plant Mol. Biol. 11: 651-662), root-specific promoters, such as ARSK1, and those disclosed in U.S. Pat. Nos. 5,618,988, 5,837,848 and 5,905,186, epidermis-specific promoters, including CUTI (Kunst et al. (1999) Biochem. Soc. Trans. 28: 651-654), pollen-active promoters such as PTA29, PTA26 and PTA13 (U.S. Pat. No. 5,792,929), promoters active in vascular tissue (Ringli and Keller (1998) Plant Mol. Biol. 37: 977-988), flower-specific (Kaiser et al. (1995) Plant Mol. Biol. 28: 231-243), pollen (Baerson et al. (1994) Plant Mol. Biol. 26: 1947-1959), carpels (Ohl et al. (1990) Plant Cell 2: 837-848), pollen and ovules (Baerson et al. (1993) Plant Mol. Biol. 22: 255-267), auxin-inducible promoters (such as that described in van der Kop et al. (1999) Plant Mol. Biol. 39: 979-990 or Baumann et al. (1999) Plant Cell 11: 323-334), cytokinin-inducible promoter (Guevara-Garcia (1998) Plant Mol. Biol. 38: 743-753), promoters responsive to gibberellin (Shi et al. (1998) Plant Mol. Biol. 38: 1053-1060, W[upsilon]lmott et al. (1998) Plant Mol. Biol. 38: 817-825) and the like. Additional promoters are those that elicit expression in response to heat (Ainley et al. (1993) Plant Mol. Biol. 22: 13-23), light (e.g., the pea rbcS-3A promoter, described in Kuhlemeier et al. (1989) Plant Cell 1: 471-478, and the maize rbcS promoter, described in Schaffner and Sheen (1991) Plant Cell 3: 997-1012); wounding (e.g., wunl, described in Siebertz et al. (1989) Plant Cell 1: 961-968), pathogens (such as the PR-I promoter described in Buchel et al. (1999) Plant Mol. Biol. 40: 387-396, and the PDFI 0.2 promoter described in Manners et al. (1998) Plant Mol. Biol. 38: 1071-1080), and chemicals such as methyl jasmonate or salicylic acid (Gatz (1997) Annu. Rev. Plant Physiol. Plant Mol. Biol. 48: 89-108). In addition, the timing of the expression can be controlled by using promoters such as those acting at senescence (Gan and Amasino (1995) Science 270: 1986-1988); or late seed development (Odell et al. (1994) Plant Physiol. 106: 447-458).

The polynucleotides and polypeptides of this invention can also be expressed in a plant in the absence of an expression cassette by manipulating the activity or expression level of the endogenous gene by other means, such as, for example; by ectopically expressing a gene by T-DNA activation tagging (Ichikawa et al. (1997) Nature 390 698-701; Kakimoto et al. (1996) Science 21 A: 982-985). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (for example, in PCT Publications WO 96/06166 and WO 98/53057 which describe the modification of the DNA-binding specificity of zinc finger proteins by changing particular amino acids in the DNA-binding motif).

The transgenic plant can also include the machinery necessary for expressing or altering the activity of a polypeptide encoded by an endogenous gene, for example, by altering the phosphorylation state of the polypeptide to maintain it in an activated state. Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a sPLA-2 protein or its homolog, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledonous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. Examples of these protocols are described in Ammirato et al. eds., (1984) Handbook of Plant Cell Culture—Crop Species, Macmillan Publ. Co., New York N.Y.; Shimamoto et al. (1989) Nature 338: 274-276; Fromm et al. (1990) Bio/Technol. 8: 833-839; and Vasil et al. (1990) Bio/Technol. 8: 429-434.

Transformation and regeneration of both monocotyledonous and dicotyledonous plant cells are now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens*-mediate[alpha] transformation. Transformation means introducing a nucleotide sequence into a plant in a manner to cause stable or transient expression of the sequence. Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042. Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Practical and presently preferred embodiments of the present invention are illustrated as shown in the following Examples. However, it will be appreciated that those skilled in the art, on consideration of this disclosure, may make modifications and improvements within the spirit and scope of the present invention.

We have isolated two cDNA clones encoding *Arabidopsis* sPLA2 proteins (sPLA2-a and sPLA2-b) as shown in SEQ ID Nos: 1-4 and used these cDNAs for the expression of sPLA2 in the tissues of transgenic *Arabidopsis* plants under the transcriptional control of 35S promoter. We at first have biochemically characterized the sPLA2 expressing transgenic *Arabidopsis* plants and then have demonstrated that the transgenic plants have a significantly enhanced resistance against different abiotic and biotic stress conditions of very different origin.

EXAMPLE 1

Cloning of an sPLA2 cDNA from *Arabidopsis*

Using the previously described N-terminal amino acid sequence of an elm PLA2 (Stahl et al., 1998) as a query, we identified a related sequence in the *Arabidopsis* ecotype Columbia (Col-0) database (AtDB Stanford University). An *Arabidopsis thaliana* cDNA library constructed in YESTrp2 (Invitrogen, Carlsbad, CA) was obtained from Soo Young Kim (Kumho Life and Environmental Science Laboratory, Gwangju, Korea). Two PLA2-specific oligonucleotides (5'-TCGCACTTCATTGATGCG-3' (SEQ ID NO: 6) and 5'-TCATAGCTCTGTTTTCATATCATTACCT-3' (SEQ ID NO: 7)) were used in combination with the T3 and T7 promoter-specific primers to isolate partial PLA2 sequences from a cDNA library. The PCR contained 6 pmol of each primer and 1 unit of ExTaq polymerase (Pan Vera, Madison, WI) and consisted of 35 cycles of 94 C for 30 s, 60 C for 30 s, and 72 C for 1 min. Amplified products were isolated from a 0.8% (w/v) agarose gel and cloned into pGEM-T (Promega) for sequencing using the dideoxy-Sanger method, which is based on extension of oligonucleotide primers by DNA polymerase. The DNA sequences of the Arabidopsis sPLA2-a and sPLA2-b genes were deposited at NCBI GenBank as AY344842 and AF541915.

EXAMPLE 2

Figure 1:
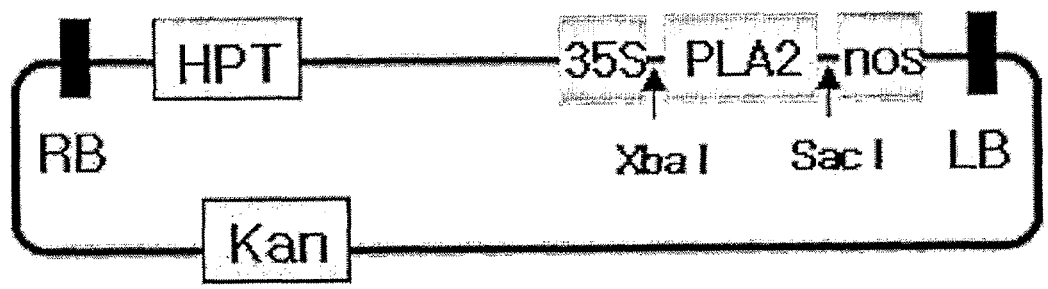
FIG. 1 depicts the genetic map of vector pBIG-HYG that was used for plant transformation.

Introduction of the sPLA2 cDNA into *Arabidopsis* Plants for Ectopic Expression of this Protein in Transgenic Tissues The applied transformation technology is based on the *Agrobacterium* gene delivery system reviewed by Hinchee et al. "Plant Cell and Tissue Culture" pp. 231-270, eds. I. K. Vasil T. A Thorpe, Kluwer Academic Publisher 1994. In the present Examples we have used the system with plant transformation vector pBIG-HYG under the control of the CaMV 35S promoter (FIG. 1). The PCR-amplified cDNAs of sPLA2-a (SEQ ID NO:1) and sPLA2-b (SEQ ID NO:3) were cloned into the XbaI and SacI sites of the binary vector pBIG (a derivative of the binary vector pB110, CLONTECH) between the CaMV 35S promoter and the nopaline synthase terminator to construct a recombinant binary vector pBIG-HYG (FIG. 1). The so constructed binary vectors were mobilized into an *Agrobacterium* strain. The flowers of *Arabidopsis* (Col-0) were then co-cultured with the *Agrobacterium* cells and transformants were selected on hygromycin-containing medium. T3 transgenic homolines were obtained from the primary transformants by sequential selection in the media containing antibiotic hygromycin and further characterized.

EXAMPLE 3

Figure 2:
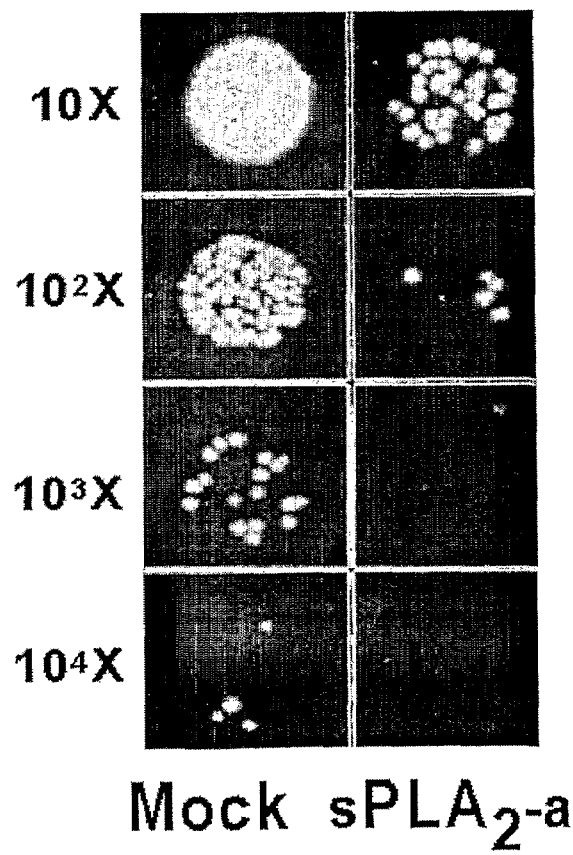
FIG. 2 depicts anti-bacterial activity against *Pseudomonase syringae* pv tomato of recombinant sPLA2-a protein.
Figure 3:
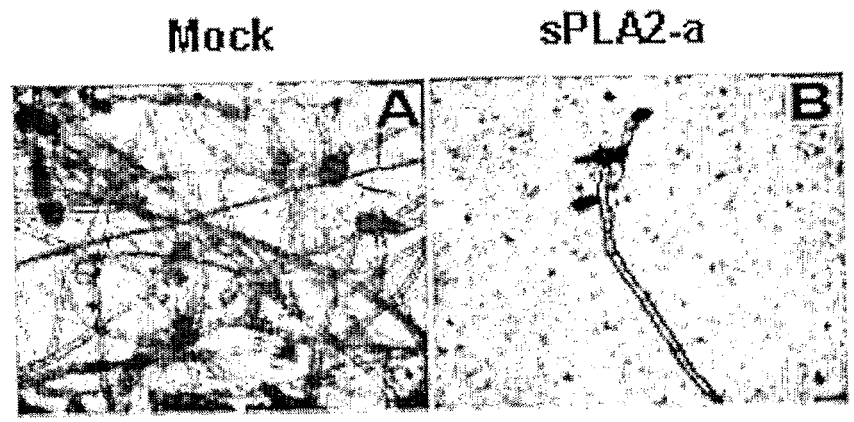
FIG. 3 depicts anti-fungal activity against *Alternaria brassicicola* of recombinant sPLA2-a protein.

Recombinant Proteins of sPLA2 have Anti-microbial Activities Against Bacteria and Fungus The free mature form (3 µg) of recombinant $PLA_2\alpha$ protein produced in BL21(DE3)PLys cells, as previously described (Lee et al., 2005), was added to virulent *Pseudomonase syringae* pv tomato ($5\times10^5$ cfu ml$^{-1}$) suspended in 100 µl of Tris.HCl (50 mM, pH 8.0) solution containing 10 mM $CaCl_2$ or to fungus (*Alternaria brassicicola*) suspended in the culture media. The mock control consisted of bacteria suspended in solution without $PLA_2\alpha$. FIG. 2 depicts anti-bacterial activity against *Pseudomonase syringae* pv tomato of recombinant sPLA2-a protein. Recombinant $sPLA_2$-a protein greatly decreases numbers of virulent bacteria (*Pseudomonas syringae*) compared to mock controls after 6 h incubation. FIG. 3 depicts anti-fungal activity against *Alternaria brassicicola* of recombinant sPLA2-a protein. Recombinant $sPLA_2$-a protein greatly inhibited the growth of fungus (*Alternaria brassicicola*) compared to mock controls after 72 h incubation.

Recombinant proteins of sPLA2-b were expressed in *E. coli* (BL21) and purified by fusion protein-affinity chromatography described by Lee et al (2003). When recombinant sPLA2-b proteins (3 µg/100 ul) were added to the culture media, those proteins showed a strong antimicrobial activity against fungus (*Fusarum oxysporum*).

TABLE 1

|  | Control ($H_2O$) | Recombinant sPLA2-b |
|---|---|---|
| Added to growth medium at 8 hr (budding point) | Vigorous growth of hyphae | Growth arrest at budding point |

Figure 4:
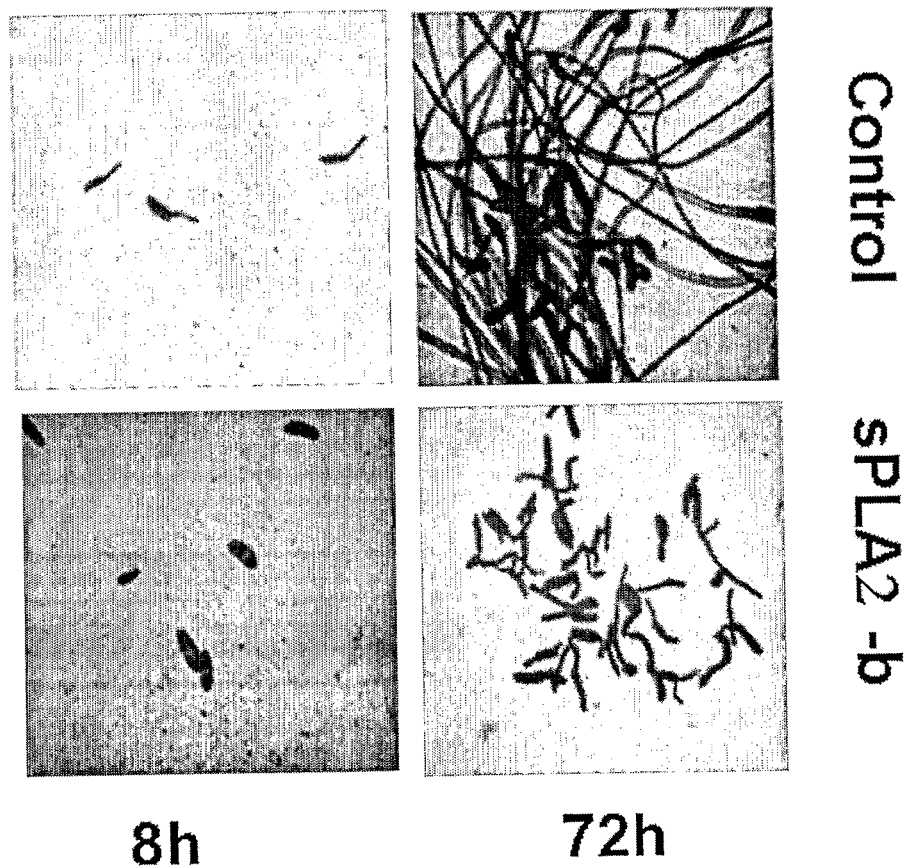
FIG. 4 depicts anti-fungal activity against *Fusarum oxysporum* of recombinant sPLA2-b protein.

FIG. 4 depicts anti-fungal activity against *Fusarum oxysporum* of recombinant sPLA2-b protein. Compared to the control (H2O) treatment, sPLA2-b protein treatment resulted in the dramatic reduction in the growth of fungus (*Fusarum oxysporum*) after 72 hr.

EXAMPLE 4

Transformed Plants Overproducing sPLA2 have Enhanced Resistance Against Fungal (*Botrytis cinerea*) Infections Since we have found that recombinant sPLA2 proteins have a strong anti-microbial activity, we have examined the enhanced resistance of transformed plants expressing the sPLA2 gene against microbial infections. First, we infected transgenic *Arabidopsis* plants with fungus *Botrytis cinerea*. Fungal suspension solutions were inoculated into the leaves of wild type and plants transformed with sPLA2-b. Four days after injection, we analyzed the degree of necrotization on leaf tissues.

TABLE 2

Effect of fungal pathogens on transformed *Arabidopsis* plants

|  | Wild type | Transformed with sPLA2-b |
|---|---|---|
| Lesion diameter (mm) | 7 ± 2 | 5 ± 1 |

Figure 5A:
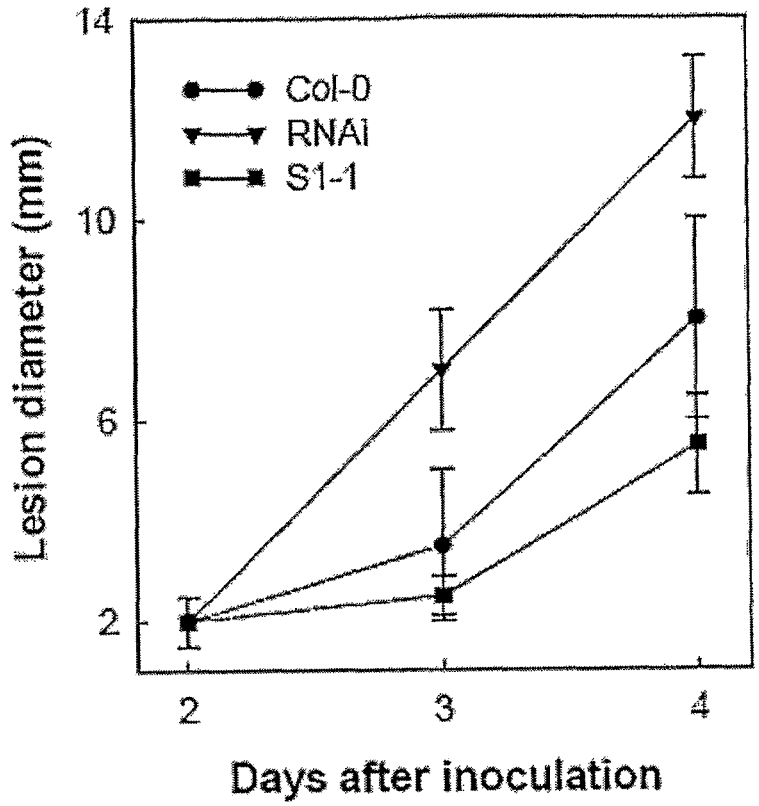
FIG. 5 depicts enhanced resistance against fungal (*Botrytis cinerea*) infections of transformed plants overproducing sPLA2-b.
Figure 5B:
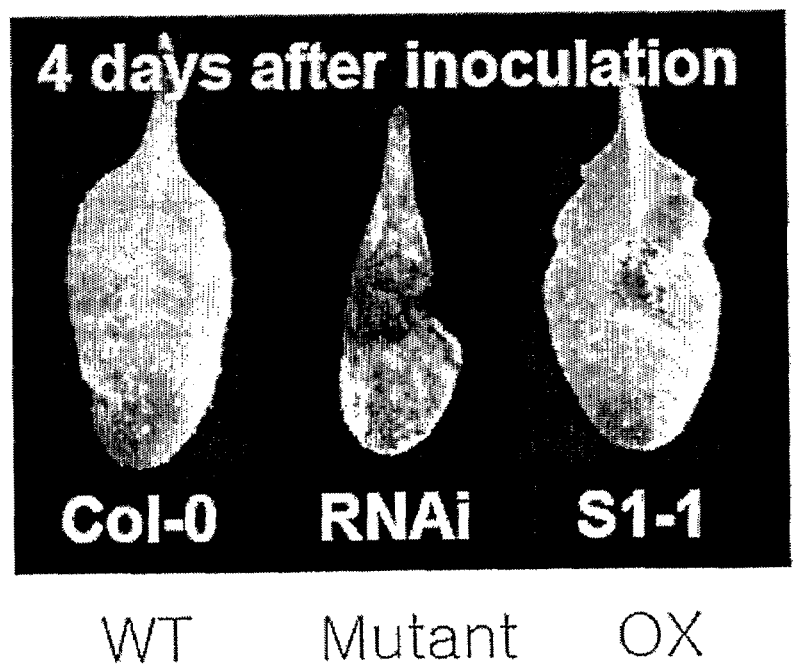

The presented data show significant reduction of necrotization on the leaves of the transformed plants. These results promise enhanced resistance against damages caused by fungal infections. FIG. 5 depicts enhanced resistance against fungal (*Botrytis cinerea*) infections of transformed plants overproducing sPLA2-b. Plants transformed with sPLA2-b (S1-1) showed significant reduction of necrotization on the leaves compared to wild type (Col-0) or RNAi-silenced plants.

EXAMPLE 5

Transformed *Arabidopsis* Plants Overproducing sPLA2 have Enhanced Resistance against Bacterial Pathogen *Pseudomonas syringae* pv. Tomato Strain DC3000

Transformed *Arabidopsis* plants overexpressing sPLA2-a or sPLA2-b are vacuum infilterated with $5\times10^4$ cfu/ml of virulent bacterial pathogen *Pseudomonas syringae* pv. tomato strain DC3000. Four days after infilteration, bacterial growth was determined and compared between control and transformed plants.

TABLE 3

|  | Wild type | Transformed with sPLA2-b |
|---|---|---|
| Bacterial growth (cfu/ml) | $6 \times 10^6$ | $1 \times 10^6$ |

Figure 6:
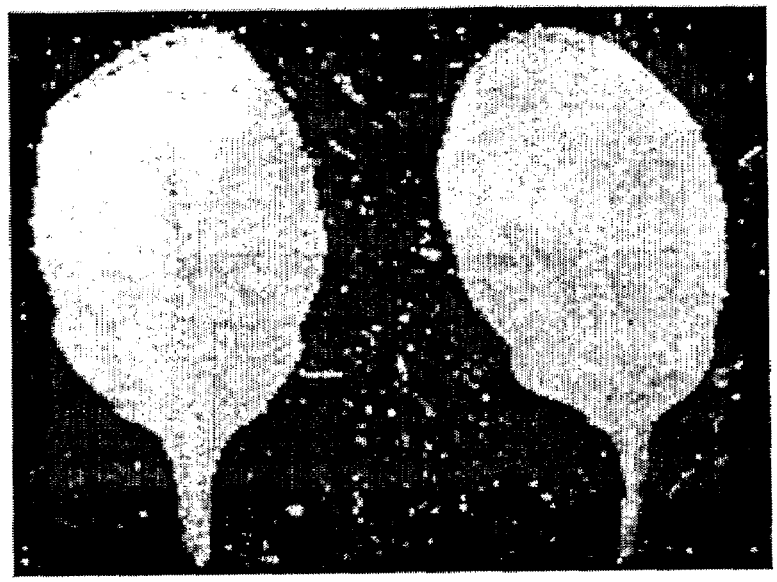
FIG. 6 depicts enhanced resistance against bacterial pathogen *Pseudomonas syringae* pv. tomato strain DC3000 of transformed plants overproducing sPLA2-a.
Figure 6:
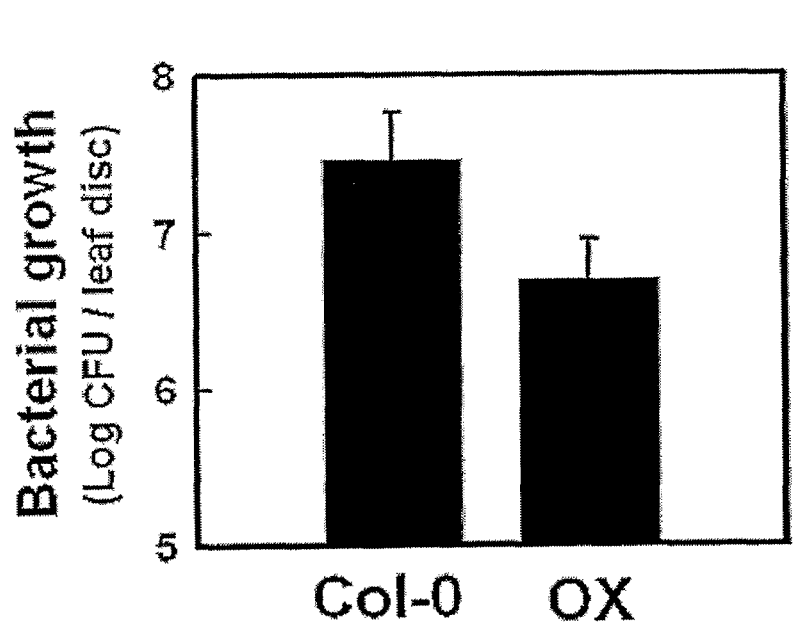

FIG. 6 depicts enhanced resistance against bacterial pathogen *Pseudomonas syringae* pv. tomato strain DC3000 of transformed plants overproducing sPLA2-a. The transformed lines expressing the sPLA2-a gene under the control of the CaMV35S promoter (sPLA2-a OX) also showed a significant reduction in bacterial growth.

EXAMPLE 6

Transformed Tobacco Plants Overproducing sPLA2 have Enhanced Resistance Against Bacterial (*Pseudomonas syringae* pv. *tabaci*) Infections To generate local transformed plants, five weeks old tobacco plant leaves were infilterated with a suspension of *Agrobacterium tumefaciens* carrying a binary vector pBIG expressing sPLA2-b at $1\times10^7$ CFU/ml. Control plants were infilterated with a suspension of *Agrobacterium tumefaciens* carrying a binary vector pBIG itself. The plants were incubated for three days under green house. Local transformed leaves were then inoculated 10 mM $MgCl_2$ containing *Pseudomonas syringae* pv. *tabaci* ($1\times10^6$ CFU/ml) at the location of transient gene expression. Disease symptoms were compared between the control and sPLA2-b-overexpressing leaves 5 days after inoculation of pathogen.

TABLE 4

|  | Transformed with vector | Transformed with sPLA2-b |
| --- | --- | --- |
| Necrotization degree | 30% (3/10 spots) | 0% (0/10 spots) |

Figure 7:
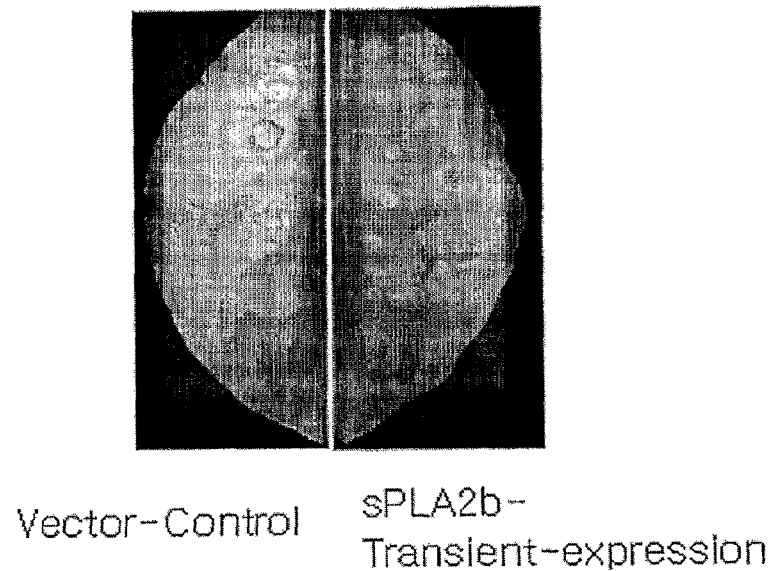
FIG. 7 depicts enhanced resistance against bacterial (*Pseudomonas syringae* pv. *tabaci*) Infections of transformed Tabacco plants overproducing sPLA2-b.

The above data demonstrates that transformed plants with sPLA2-b have a significantly enhanced resistance against the damages caused by bacterial infection. FIG. 7 depicts enhanced resistance against bacterial (*Pseudomonas syringae* pv. *tabaci*) Infections of transformed Tabacco plants overproducing sPLA2-b. Tobacco plants in which sPLA2-b is transiently expressed showed less disease symptom (necronization) compared to the control that is transformed only with vector.

EXAMPLE 7

Transformed *Arabidopsis* Plants Overproducing sPLA2-a have Enhanced Resistance against Bacterial Pathogen *Erwinia*

Figure 8A:
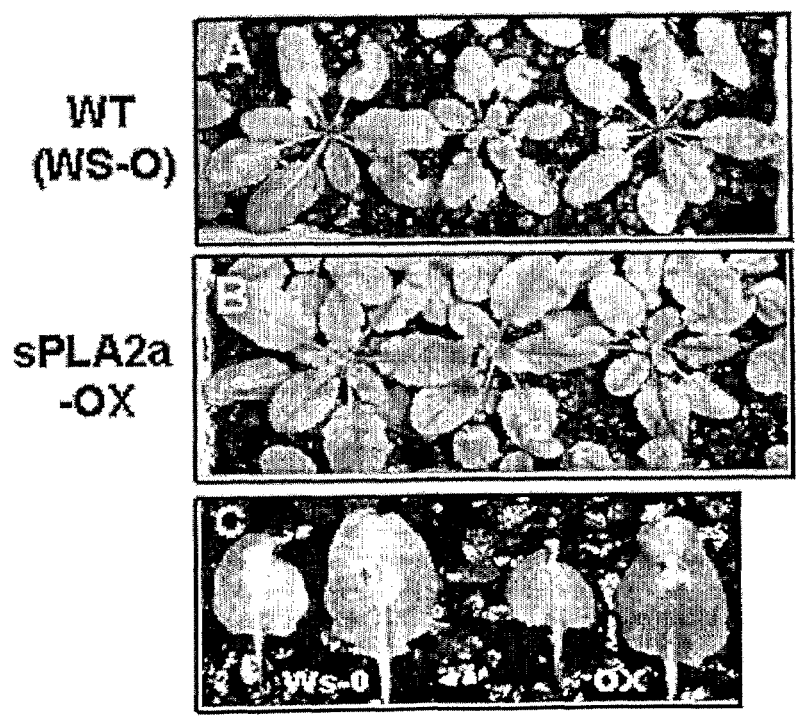
FIG. 8 depicts enhanced resistance against bacterial pathogen *Erwinia* of transformed *Arabidopsis* plants overproducing sPLA2-a.
Figure 8B:
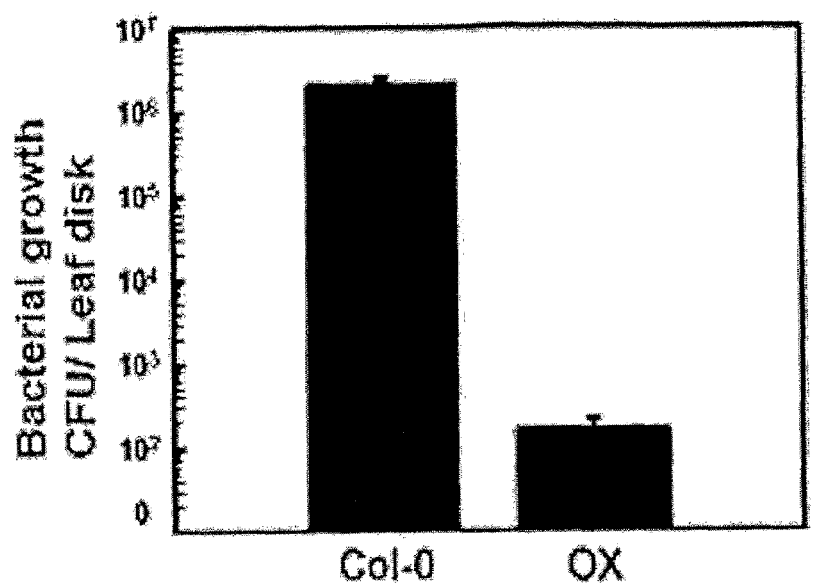

Transformed *Arabidopsis* plants overexpressing sPLA2-a are vacuum infilterated with $5\times10^4$ cfu/ml of virulent bacterial pathogen *Erwinia* strain. Four days after infilteration, bacterial growth was determined and compared between control and transformed plants. FIG. 8 depicts enhanced resistance against bacterial pathogen *Erwinia* of transformed *Arabidopsis* plants overproducing sPLA2-a. The transformed lines expressing the sPLA2-a gene (sPLA2-a OX) showed a significant reduction in *Erwinia* growth compared to wild type (WS-O).

EXAMPLE 8

Transformed *Arabidopsis* Plants Overproducing sPLA2 have Enhanced Resistance against fungal pathogen *Peronospora parasitica*

Figure 9A:
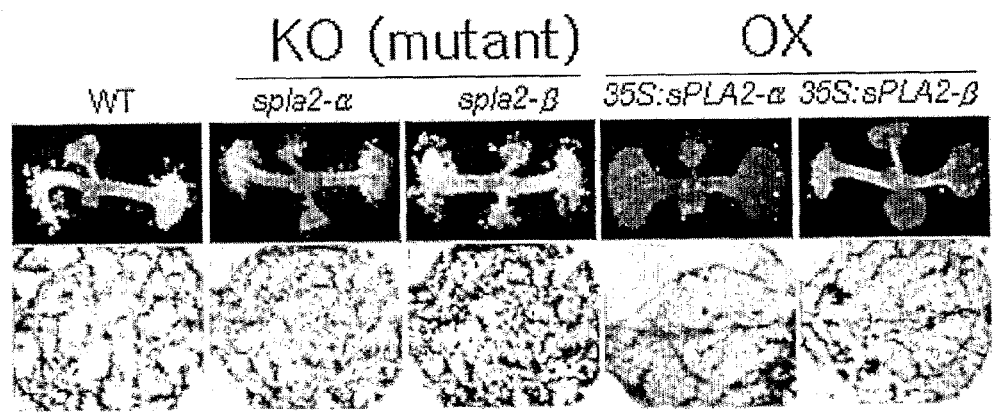
FIG. 9 depicts enhanced resistance against fungal pathogen *Peronospora parasitica* of transformed *Arabidopsis* plants overproducing sPLA2.
Figure 9B:
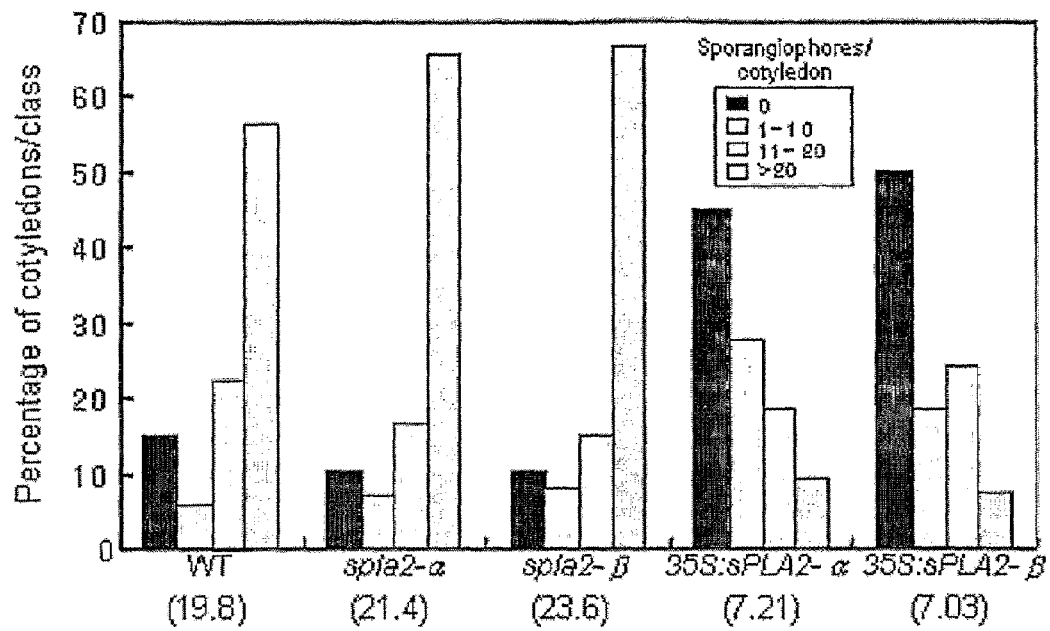

Transformed *Arabidopsis* plants overexpressing sPLA2-a or sPLA2-b are infected by spraying suspension of *Peronospora parasitica*. Seven days after infection, fungal growth was determined and compared between wild type (WT), knockout mutant (KO), and sPLA2-a or sPLA2-b overexpressing plants (OX). FIG. 9 depicts enhanced resistance against fungal pathogen *Peronospora parasitica* of transformed *Arabidopsis* plants overproducing sPLA2. The transformed lines expressing the sPLA2-a or sPLA2-b gene (OX) showed much lower percentages of sporangiophores 7 days after infection of *Peronospora parasitica* compared to wild type (WT). ( ) indicates average number of sporangiophores/cotyledon. The average numbers of sporangiophores per cotyledon are about 7 in the transgenic plants compared to about 20 in wild type plants.

EXAMPLE 9

Transformed *Arabidopsis* Plants Overproducing sPLA2-a have Enhanced Resistance against Fungal Pathogen *Botrytis cynerea*

Figure 10:
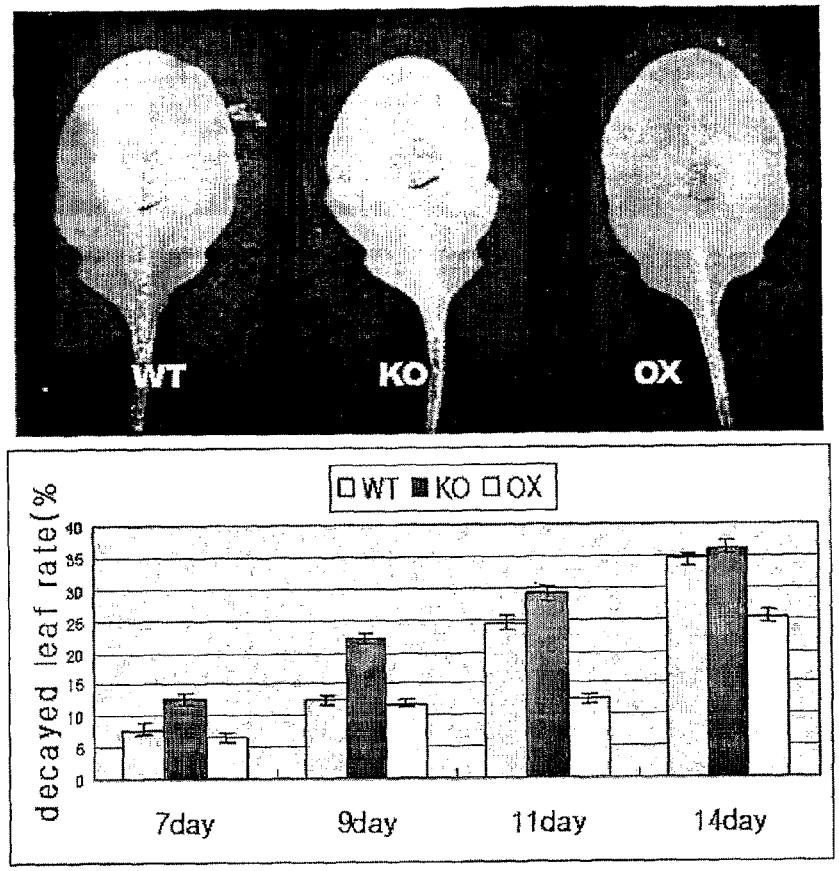
FIG. 10 depicts enhanced resistance against fungal pathogen *Botrytis cynerea* of transformed *Arabidopsis* plants overproducing sPLA2-a.

Transformed *Arabidopsis* plants overexpressing sPLA2-a are infected by spraying suspension of *Botrytis cynerea*. Seven to fourteen days after infection, decayed leaf rates by fungal infection were determined and compared between wild type (WT), knockout mutant (KO), and sPLA2-a overexpressing plants (OX). FIG. 10 depicts enhanced resistance against fungal pathogen *Botrytis cynerea* of transformed *Arabidopsis* plants overproducing sPLA2-a. The transformed lines expressing the sPLA2-a gene (OX) showed much lower decay rates 7 to 14 days after infection of *Botrytis cynerea* compared to wild type (WT) and knockout mutant (KO).

EXAMPLE 10

Transformed Plants Overproducing sPLA2 have Enhanced Resistance Against Abiotic (Salt) Stress and Accelerated Recovery Transgenic *Arabidopsis* plants overexpressing sPLA2-b were grown in the 1×MS medium containing 20 mM NaCl for 7 days. The plants were then transferred to regular 1×MS medium in order to let the plants recover from salt stress injury and kept growing further for 12 days.

TABLE 5

|  | Control Wild type | Transformed with sPLA2-b | |
| --- | --- | --- | --- |
|  | (Col-0) | line 1-1 | line 6-8 |
| Injured plants after 7 days (%) | 85% | 75% | 40% |
| Recovered plants after 12 days (%) | 5% | 50% | 70% |

Figure 11:
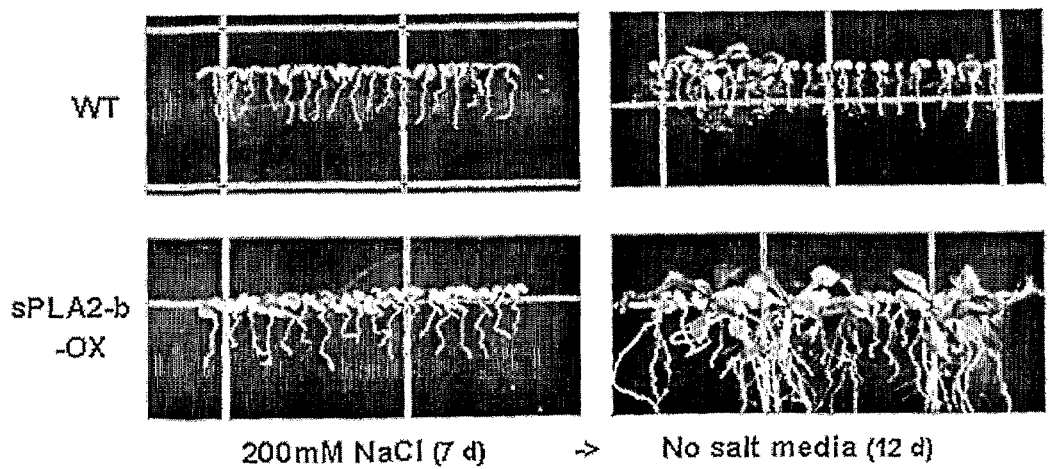
FIG. 11 depicts enhanced resistance against abiotic (salt) stress and accelerated recovery of transformed plants overproducing sPLA2-b.

The above data demonstrates that transgenic plants overexpressing sPLA2-b have not only a considerably enhanced resistance against salt stress but also dramatically enhanced recovery ability after returning to the normal growth conditions. FIG. 11 depicts enhanced resistance against abiotic (salt) stress and accelerated recovery of transformed plants overproducing sPLA2-b. The transformed lines expressing the sPLA2-b gene (OX) showed more resistance to salt stress (200 mM NaCl) and better recovery from injury when they are transferred to the media without salt compared to wild type (WT).

EXAMPLE 11

Transformed Plants Overproducing sPLA2-b have Enhanced Ability of Early Flowering Transgenic *Arabidopsis* plants overexpressing sPLA2-b were grown in the soil mixture (vermiculite:perlite:peat 2:1:1 v/v/v) at 22° C. in growth rooms programmed for a 12 hr light (90 μE/m/s) and 12 hr dark cycle. The flowering time of the transgenic plants were compared to Col-0 wild type plants.

TABLE 6

|  | Wild type | Transformed with sPLA2-b |
|---|---|---|
| Flowering days after germination | 27 ± 3 | 20 ± 2 |

Figure 12:
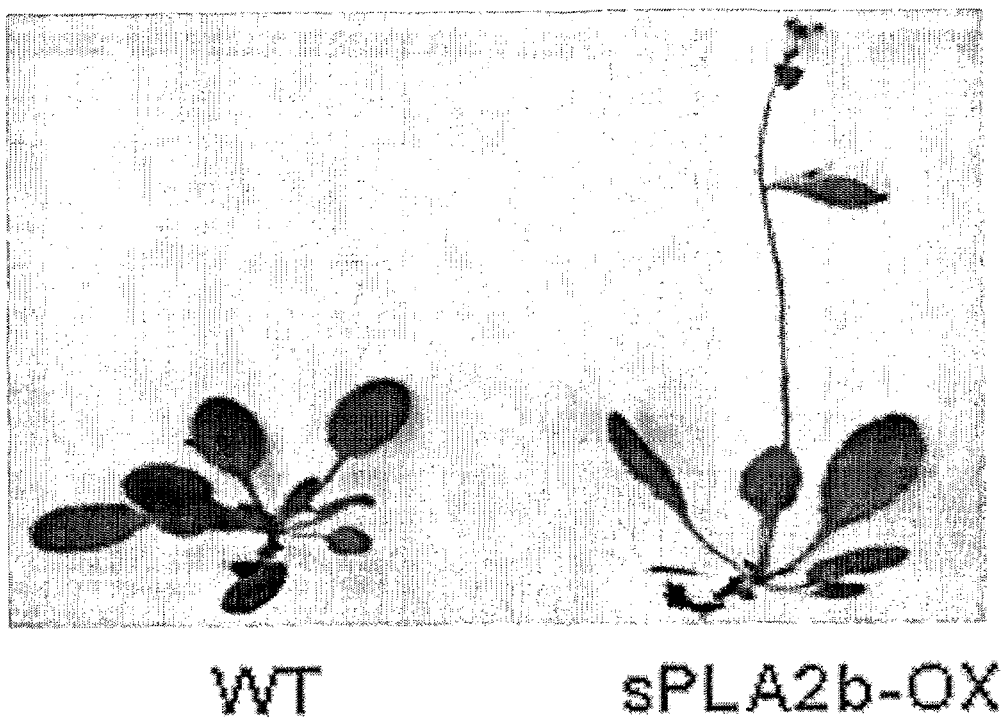
FIG. 12 depicts enhanced early flowering ability of transformed plants overproducing sPLA2-b.

The above data demonstrates that transgenic plants overexpressing PLA2-b have a significantly enhanced ability of early flowering. FIG. 12 depicts enhanced early flowering ability of transformed plants overproducing sPLA2-b. The transformed lines expressing the sPLA2-b gene (OX) showed earlier flowering compared to wild type (WT).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for producing a transgenic plant having a resistance to high salt-induced osmotic abiotic stress and biotic stress selected from the group consisting of diseases caused by the genus *Fusarium, Peronospora, Alternaria, Botrytis, Pseudomonas* or *Erwinia*, which comprises the steps of:
   (a) transforming a target plant with an expression vector comprising a polynucleotide encoding a sPLA2 protein having the amino acid sequence of SEQ ID NO:4; wherein the expression vector further comprises a regulatory element operably linked to the polynucleotide; and
   (b) selecting a transgenic plant that is more resistant to the abiotic and biotic stresses than an untransformed wild type plant.

2. The method of claim 1, wherein the polynucleotide comprises the nucleotide sequence of SEQ ID NO: 3.

3. The method of claim 1, wherein the expression vector under the control of a CaMV 35S promoter.

4. A method for increasing the resistance to high salt-induced osmotic abiotic stress and biotic stress selected from the group consisting of diseases caused by the genus *Fusarium, Peronospora, Alternaria, Botrytis, Pseudomonas* or *Erwinia*, which comprises the steps of:
   (a) transforming a target plant with an expression vector comprising a polynucleotide encoding a sPLA2 protein having the amino acid sequence of SEQ ID NO:4; wherein the expression vector further comprises a regulatory element operably linked to the polynucleotide; and
   (b) selecting a transgenic plant that is more resistant to the abiotic and biotic stresses than an untransformed wild type plant.

5. The method of claim 4, wherein the polynucleotide comprises the nucleotide sequence of SEQ ID NO: 3.

* * * * *

UNITED STATES PATENT AND TRADEMARK OFFICE
CERTIFICATE OF CORRECTION

PATENT NO. : 8,203,031 B2
APPLICATION NO. : 12/527323
DATED : June 19, 2012
INVENTOR(S) : Ryu et al.

It is certified that error appears in the above-identified patent and that said Letters Patent is hereby corrected as shown below:

On the Title Page, in Item (54) and in the Specification, Column 1, lines 1-4, Title, replace "TRANSGENIC PLANS EXHIBITING INCREASED RESISTANCE TO BIOTIC AND ABIOTIC STRESSES AND METHODS FOR PRODUCING THE SAME"

with

--TRANSGENIC PLANS EXHIBITING INCREASED RESISTANCE TO BIOTIC AND ABIOTIC STRESSES OR ACCELERATED FLOWERING TIME AND METHODS FOR PRODUCING THE SAME--.

In the Specification

Column 2, Line 11, replace "stablizing" with --stabilizing--;

Line 53, replace "Throughtout" with --Throughout--.

Column 6, Line 47, replace "inspecific" with --nonspecific--.

Column 9, Line 7, replace "Ti plasmid of, *Agrobacterium*" with --Ti plasmid of *Agrobacterium*--.

Column 12, Line 9, replace "Tabacco" with --Tobacco--.

Column 14, Line 49, replace "infilterated" with --infiltrated--;

Line 51, replace "infilteration" with --infiltration--.

Signed and Sealed this
Eleventh Day of March, 2014

Michelle K. Lee
*Deputy Director of the United States Patent and Trademark Office*

CERTIFICATE OF CORRECTION (continued)
U.S. Pat. No. 8,203,031 B2

Column 15, Line 8, replace "infilterated" with --infiltrated--;

Line 31, replace "Tabacco" with --Tobacco--;

Lines 32-33, replace "(necronization)" with --necrotization--;

Line 44, replace "infilterated" with --infiltrated--;

Line 45, replace "infilteration" with --infiltration--.

In the Claims

Column 21, Claim 1, Line 28, replace "*Botrvtis*" with --*Botrytis*--.